United States Patent [19]
Kocal et al.

[11] Patent Number: 5,276,231
[45] Date of Patent: Jan. 4, 1994

[54] ALKYLAROMATIC PROCESS WITH REMOVAL OF AROMATIC BY-PRODUCTS

[75] Inventors: Joseph A. Kocal, Gurnee; Donald J. Korous, Bensenville, both of Ill.

[73] Assignee: UOP, Des Plaines, Ill.

[21] Appl. No.: 919,311

[22] Filed: Jul. 27, 1992

[51] Int. Cl.$^5$ .......................... C07C 2/66; C07C 2/68
[52] U.S. Cl. .................................. 585/323; 585/259; 585/315; 585/319; 585/324; 585/467; 585/804
[58] Field of Search ............... 585/315, 319, 323, 324, 585/259, 467, 804

[56] References Cited
U.S. PATENT DOCUMENTS
5,019,662  5/1991  Vora et al. ......................... 585/323

Primary Examiner—Anthony McFarlane
Attorney, Agent, or Firm—Thomas K. McBride; Eugene I. Snyder

[57] ABSTRACT

An improved process for the production of alkylated aromatic compounds by paraffin dehydrogenation and aromatic alkylation is disclosed. Aromatic by-products normally formed in paraffin dehydrogenation are selectively removed using at least one aromatics removal zone. Removal of these aromatic by-products significantly reduces the deactivation rate of solid alkylation catalysts. The improved process produces a detergent alkylate product that is significantly more linear than that produced by the prior art process.

25 Claims, 1 Drawing Sheet

ALKYLAROMATIC PROCESS WITH REMOVAL OF AROMATIC BY-PRODUCTS

FIELD OF THE INVENTION

The invention is an improvement in a process for the production of alkylated aromatic compounds.

BACKGROUND OF THE INVENTION

Nearly thirty years ago it became apparent that household laundry detergents made of branched alkylbenzene sulfonates were gradually polluting rivers and lakes. Solution of the problem led to the manufacture of detergents made of linear alkylbenzene sulfonates (LABS), which were found to biodegrade more rapidly than the branched variety. Today, detergents made of LABS are manufactured world-wide.

LABS are manufactured from linear alkyl benzenes (LAB). The petrochemical industry produces LAB by dehydrogenating linear paraffins to linear olefins and then alkylating benzene with the linear olefins in the presence of HF. This is the industry's standard process. Over the last decade, environmental concerns over HF have increased, leading to a search for substitute processes employing catalysts other than HF that are equivalent or superior to the standard process. Four of the chief criteria for a substitute process are: extent of conversion, selectivity to monoalkylbenzene, linearity of alkylbenzene, and catalyst deactivation rate. At this point, it is useful for the sake of clarity later to define these terms.

i. Alkylation conversion

In alkylation benzene typically is supplied in excess, and therefore conversion is defined in terms of the olefin. The degree of conversion at a constant ratio of excess benzene relative to olefin and a constant temperature is a measure of a catalyst's activity in a process. The degree of conversion may be expressed by the formula, $$V = C/T * 100.$$

where V equals percent conversion, C equals moles of olefin consumed, and T equals moles of olefin initially present.

ii. Alkylation selectivity

Selectivity is defined as the percentage of total olefin consumed under reaction conditions which appears as monoalkylbenzene and can be expressed by the equation, $$S = M/C * 100,$$

where S equals percent selectivity, M equals moles of monoalkylbenzenes produced, and C equals moles olefin consumed. The higher the selectivity, the more desirable the process. An approximate measure of selectivity is given by the equation, $$S = (\text{weight monoalkylbenzene})/(\text{weight total products}) * 100$$

where "total products" includes monoalkylbenzenes, polyalkylbenzenes, and olefin oligomers. At high selectivity ($S \leq 85\%$) the results calculated from the two equations are nearly identical. The latter of the foregoing two equations is routinely used in commercial practice because of the difficulty in distinguishing between oligomers and polyalkylbenzenes.

iii. Linearity

The reaction of linear olefins with benzene in principal proceeds according to the equation, $$C_6H_6 + R_1CH=CHR_2 \rightarrow C_6H_5CH(R_1)CH_2R_2 + C_6H_5CH(R_2)CH_2R_1.$$

Note that the side chain is branched solely at the benzylic carbon and contains only one branch in the chain. Although strictly speaking this is not a linear alkylbenzene, the terminology which has grown up around the process and product in fact includes as linear alkylbenzenes those materials whose alkyl group chemically arises directly from linear olefins and therefore includes alpha-branched alkylbenzenes. Because alkylation catalysts also may induce the rearrangement of olefins to give products which are not readily biodegradable, for example, alpha, alpha-disubstituted olefins which subsequently react with benzene to afford an alkyl benzene with branching at other than the benzylic carbon, the degree to which the catalyst effects formation of linear alkyl benzenes is another important catalyst parameter. The degree of linearity can be expressed by the equation, $$D = L/M * 100,$$

where D equals degree of linearity, L equals weight of linear monoalkyl benzene produced, and M equals weight of monoalkyl benzene produced.

iv. Catalyst Deactivation Rate

Alkylation processes, with either HF or substitute catalysts for HF, are subject to catalyst deactivation. Whereas an alkylation process employing HF typically employs an HF regenerator, an alkylation process employing a substitute catalyst such as a solid alkylation catalyst typically includes means for periodically taking the catalyst out of service and regenerating it by removing the gum-type polymers that accumulate on the surface of the catalyst and block reaction sites. For a solid alkylation catalyst, therefore, the catalyst life is measured in terms of time in service at constant conversion between regenerations. The longer the time between regenerations, the more desirable the catalyst and the process.

Of these criteria, the linearity criterion is assuming added importance and significance in view of the expectation in some areas of minimum standards for linearity in detergents of 92-95% near-term, increasing to 95-98% by about the year 2000. Our solution to the problem of identifying a process for detergent alkylation which meets the increasingly stringent requirements of linearity began with our observation that the isomerization of linear olefins to non-linear olefins—this is the process ultimately responsible for non-linear detergent alkylate arising from a linear olefin feedstock—is quite sensitive to temperature but relatively insensitive to the particular catalyst for the detergent alkylate process. This result suggested that effecting alkylation at a lower temperature was the key to greater product linearity. Our focus then shifted to finding a substitute process with a catalyst other than HF that would catalyze detergent alkylation at lower temperatures. Paradoxically, alkylation processes that employ catalysts other than HF, that is, commercially available solid alkylation catalysts, tend to operate at higher alkylation temperatures than processes that employ HF. One reason is that solid alkylation catalysts tend to deactivate faster as alkylation temperatures decrease and therefore alkylation temperatures must be increased to meet the catalyst life requirement. A second reason is that commercially available solid alkylation catalysts are less active than HF and therefore alkylation temperatures must be increased to meet the conversion requirement.

Surprisingly, our solution to this dilemma of alkylation temperature is a new process that arose from our observations of paraffin dehydrogenation. At this point, it is useful for the sake of appreciating what follows to define two terms related to paraffin dehydrogenation.

i. Dehydrogenation Conversion

The degree of conversion at constant temperature is a measure of the catalyst's activity in a dehydrogenation process. The dehydrogenation conversion may be expressed by the formula, $$Y = U/P * 100.$$

where Y equals percent conversion, U equals weight of linear paraffin consumed, and P equals weight of linear paraffin initially present.

ii. Dehydrogenation Selectivity

However high the conversion may be, a dehydrogenation process is not valuable unless it is also selective. The dehydrogenation of linear paraffins in principal proceeds according to the equation, The double bond of the product monoolefins is distributed along the chain in substantially equilibrium proportions. Because dehydrogenation catalysts also may induce further dehydrogenation as well as rearrangement to give aromatics which subsequently are alkylated by monoolefins to afford undesirable alkyl aromatic by-products with more than one alkyl group, and other heavier alkyl aromatic by-products with more than one aromatic ring, the selectivity to which the catalyst effects formation of linear monoolefins is another important process parameter. Selectivity is defined as the percentage of total linear paraffin consumed under reaction conditions which appears as linear monoolefin and can be expressed by the equation, $$W = O/U * 100.$$

where W equals percent selectivity, O equals weight of linear monoolefin produced, and U equals weight of linear paraffin consumed. The better the selectivity, the better is the process.

Our solution to identifying a process for detergent alkylation at lower alkylation temperature arose from our observation that the life of catalyst in the alkylation process is quite sensitive to dehydrogenation selectivity but relatively insensitive to the particular catalyst for the alkylation process. Our observation suggested that reducing the aromatic by-products from dehydrogenation was the key to longer catalyst life in the alkylation process. Our focus then shifted to finding a process that would reduce the aromatic by-products in the dehydrogenation product.

The importance of our observation that the aromatic by-products from dehydrogenation is a major factor in alkylation catalyst life and that the particular catalyst plays only a minor role cannot be overemphasized, for it permits one to focus solely on methods of reducing the aromatic by-products. It is well known that these aromatic by-products are formed during paraffin dehydrogenation at the conversions typical of commercial applications, and so their presence has been long recognized. But they were believed to have no effect other than on dehydrogenation selectivity and alkylation selectivity, which were not considered sufficient to justify the cost of removing the aromatic by-products. We have found that the actual effect of the aromatic by-products is much greater, because reducing them significantly lengthens the life of the solid alkylation catalyst, without the need to raise the alkylation temperature, thereby permitting LAB production at lower alkylation temperatures which in turn produces higher linearity. A result of our observation is a novel process that uses an aromatics removal zone to permit dehydrogenation at typically high conversions and to permit alkylation at substantially lower temperature than that previously attainable by the prior art process.

LAB processes are described in the book edited by R. A. Meyers entitled "Handbook of Petroleum Refining Processes" (McGraw Hill, N.Y. 1986) and "Ullmann's Encyclopedia of Industrial Chemistry," Volumes A8 and A13, Fifth Edition (VCH, Weinheim, Germany). Flow schemes are illustrated in U.S. Pat. No. 3,484,498 issued to R. C. Berg, U.S. Pat. No. 3,494,971 issued to E. R. Fenske, U.S. Pat. No. 4,523,048 issued to Vora which teaches use of a selective diolefin hydrogenation zone, and U.S. Pat. No. 5,012,021 issued to B. Vora which teaches use of a selective monoolefin hydrogenation zone. Solid alkylation catalysts are illustrated in U.S. Pat. No. 3,201,487 issued to S. Kovach et al.; U.S. Pat. No. 4,358,628 issued to L. Slaugh; U.S. Pat. No. 4,489,213 issued to S. Kovach; and U.S. Pat. No. 4,673,679 issued to D. Farcasiu. Zeolitic solid alkylation catalysts are disclosed in U.S. Pat. Nos. 3,751,506; 4,387,259; and 4,409,412.

It is well known that polynuclear aromatic compounds and aromatic compounds may be selectively removed from a hydrocarbon processing stream on suitably selected sorbents including alumina, silica gel, cellulose acetate, synthetic magnesium silicate, macroporous magnesium silicate, macroporous polystyrene gel and graphitized carbon black. All of the above-mentioned sorbents are mentioned in a book authored by Milton L. Lee et al entitled "Analytical Chemistry of Polycyclic Aromatic Compounds" and published by Academic Press, N.Y. in 1981. A wide variety of means are disclosed for removing polynuclear aromatic compounds and aromatic compounds from a hydrocarbon stream. U.S. Pat. No. 4,447,315 issued to Lamb et al. teaches a hydrocracking process wherein polynuclear aromatics are adsorbed from a liquid stream. U.S. Pat. No. 2,395,491 issued to Mavity discloses a process for removing mononuclear from polynuclear aromatic compounds. U.S. Pat. No. 2,983,668 issued to Hemminger teaches use of a molecular sieve or silica gel to remove aromatics or n-paraffins from a reaction mix. U.S. Pat. No. 3,340,316 issued to Wackher et al. and U.S. Pat. No. 3,689,404 issued to Hofer et al. teach removal of hydrocarbons using activated carbon.

All of the above references are silent about the effect of aromatic by-products formed during paraffin dehydrogenation on the activity and lifetime of catalysts, especially solid alkylation catalysts, used in LAB processes.

BRIEF SUMMARY OF THE INVENTION

The purpose of this invention is to provide an improved process where aromatic by-products that are normally present in a stream that arises from the dehydrogenation of paraffins are selectively removed at least in part prior to the stream being used as a feedstock for the alkylation of an aromatic compound. In one embodiment, the aromatic by-products are selectively removed from a dehydrogenated product stream produced directly by the dehydrogenation zone. In another embodiment, the aromatic by-products are selectively removed from a stream, obtained from the selective alkylation zone, which contains unreacted paraffins and the aromatic by-products and which is usually recycled to the dehydrogenation zone. In yet another embodiment, diolefins in the dehydrogenated product stream are selectively hydrogenated to monoolefins and the aromatic by-products are subsequently selectively removed prior to the selective alkylation zone. In a more specific embodiment, the aromatic by-products are selectively removed by sorptive separation where the sorbent is a molecular sieve. In a still more specific embodiment the molecular sieve is 13X zeolite. In a different specific embodiment, the aromatic by-products are selectively removed by liquid-liquid extraction. Other embodiments and purposes will become clear from the ensuing discussion.

Our invention has several objectives. It is the primary objective of our invention to reduce the deactivation rate of alkylation catalysts. It is a further objective to increase alkylation selectivity and thereby reduce the amount of heavy alkylate which is produced. It is an additional objective to prevent the aromatic by-products from accumulating in the prior art processes to unacceptable concentrations. Our invention has the same objectives set forth above regardless of whether the subject process employs HF or solid alkylation catalyst. Whereas our invention reduces the catalyst deactivation rate and thereby increases the yield of linear alkylated aromatics where solid alkylation catalyst is employed, where HF is employed our invention is believed to reduce the rate of degradation of acid strength and thereby decrease regeneration requirements.

DETAILED DESCRIPTION OF THE INVENTION

It is well known that aromatic by-products are formed during the catalytic dehydrogenation of paraffins. Surprisingly, we have found that the aromatic by-products have a detrimental effect on the deactivation rate of solid alkylation catalysts in the selective alkylation zone. We have found that a process which eliminates or significantly reduces the aromatic by-products in the prior art processes reduces the deactivation rate of solid alkylation catalysts thereby allowing solid alkylation catalysts to operate at a lower temperature and to produce a significantly higher yield of linear alkylated aromatic compounds than the prior art processes. It will become clear that our invention has significant adjunct benefits as well.

We shall first describe a typical process for the production of alkylated aromatic compounds as currently and previously practiced by the prior art along with some common variants of particular interest in order to properly set the stage upon which our invention is practiced and to emphasize that the success of our invention is not dependent upon the particular variant of the prior art used. We shall then describe the improvement which is our invention where it will become clear that its success is independent of the details of the prior art processes in which it is embedded.

The two feed compounds consumed in the subject process are a paraffinic and an aromatic compound. The paraffinic feed is preferably a straight chain (unbranched) or normal paraffin having from 6 to 22 carbon atoms per molecule. A better quality detergent precursor normally results from the use in the selective alkylation zone of an olefin having from about 10 to 15 carbon atoms per molecule. Therefore, a preferred paraffinic feed is a $C_{10}$ to $C_{15}$ paraffin or a $C_{10}$-plus linear paraffin. The paraffinic feed is normally a mixture of paraffins having different carbon numbers. A preferred method for the production of the paraffinic feed is the extraction of straight chain hydrocarbons from a hydrotreated kerosene boiling range petroleum fraction. Suitable paraffinic feeds include $C_{10}$-$C_{22}$ linear paraffins, $C_{10}$-$C_{15}$ linear paraffins, and $C_{15}$-$C_{20}$ linear paraffins. In other applications of the subject process, the preferred paraffinic feed is a mixture of branched chain paraffinic compounds. These branched chain paraffinic feeds can be obtained by extraction or by suitable oligomerization and treatment processes. The aromatic feed which is alkylated in the subject process is preferably benzene, but the aromatic feed may also be of a higher molecular weight, such as toluene, a xylene, ethylbenzene, phenol, naphthalene, etc.

Figure 1:
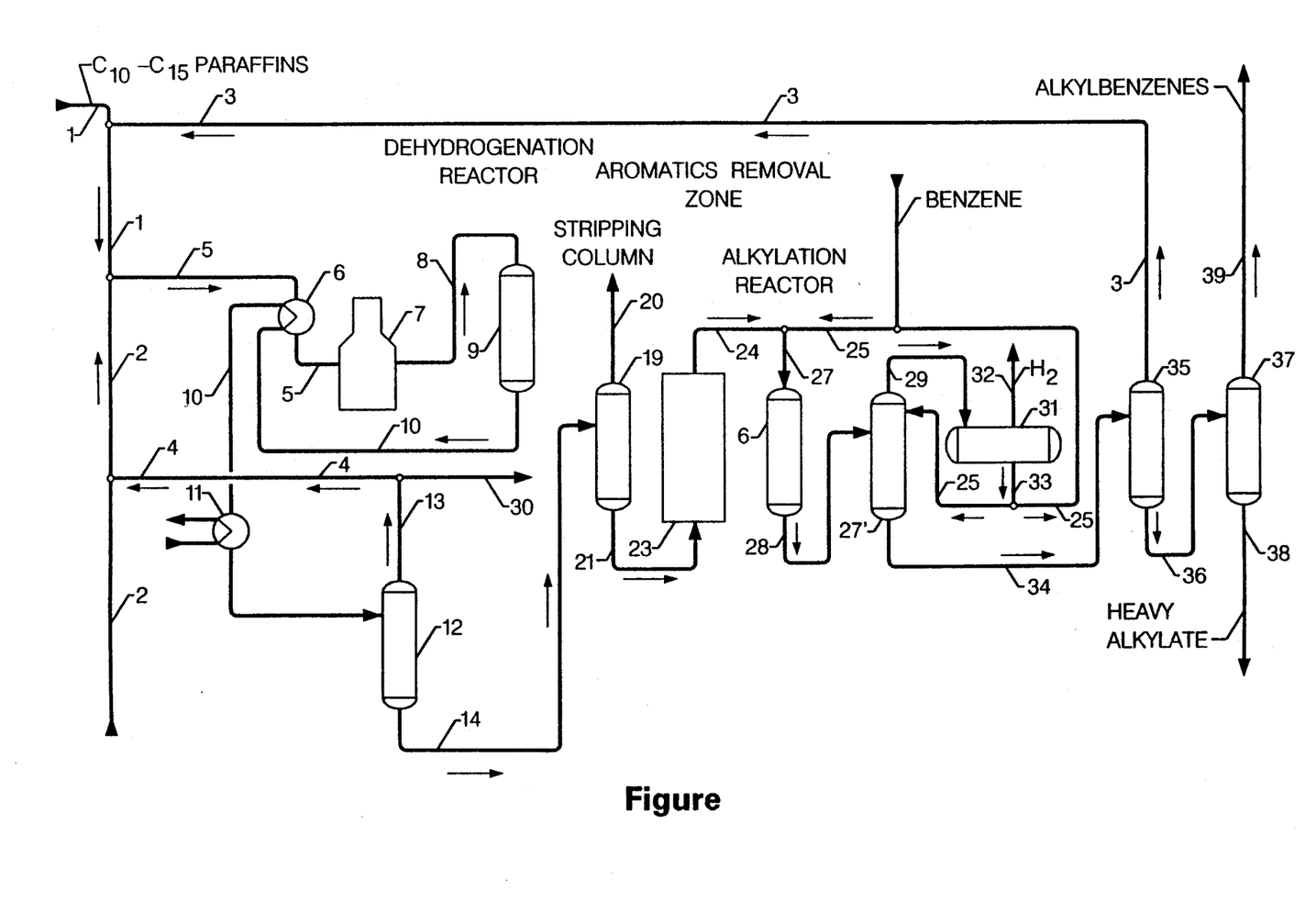
The drawing is a simplified process flow diagram of a process for the production of alkylated aromatic compounds arranged with an aromatics removal zone in accord with a preferred embodiment of the invention.

For purposes of discussion, the subject process may be divided into a dehydrogenation section and an alkylation section. The dehydrogenation section will preferably be configured substantially in the manner shown in the drawing. In this arrangement, a feed stream containing paraffins combines with recycled hydrogen and recycled unreacted paraffins from the alkylation section. This forms a reactant stream which is heated and passed through a bed of a suitable catalyst maintained at the proper dehydrogenation conditions of temperature, pressure, etc. The effluent of this catalyst bed or reactor effluent stream is usually cooled, partially condensed, and passed to a vapor-liquid or product separator. The condensed material, referred to herein as the dehydrogenated product stream, is passed to a stripping separation zone which usually includes a stripping column that removes all compounds which are more volatile than the lightest normal hydrocarbon which it is desired to charge to the alkylation section of the process. The stripping column produces a net bottoms stream referred to herein as the stripping effluent stream.

Dehydrogenation catalysts are well known in the prior art as exemplified by U.S. Pat. Nos. 3,274,287; 3,315,007; 3,315,008; 3,745,112; and 4,430,517. What is important is that catalysts for dehydrogenation are well known to those skilled in the dehydrogenation art and need not be described here in great detail. We emphasize that the nature of the dehydrogenation catalyst is not critical to the success of our invention and is largely a matter of choice to be made by the practitioner.

The stripping effluent stream is passed to an alkylation section which comprises a selective alkylation zone and a fractionation or alkylate recovery zone. In the selective alkylation zone, linear olefins in the stripping effluent stream react with a feed stream containing an aromatic which is generally benzene to produce a selective alkylation zone effluent stream containing linear alkylbenzene. The selective alkylation zone can have a number of different configurations and reactor vessels depending on whether the catalyst is HF or a solid alkylation catalyst. Solid alkylation catalysts typically are characterized as having an acid function and are, therefore, better known as solid acid catalysts. Such solid acid catalysts include, but are not limited to, materials such as amorphous silica-alumina, crystalline aluminosilicate materials such as zeolites and molecular sieves, naturally occurring and man-made clays including pillared clays, sulfated oxides such as sulfonated zirconia, traditional Friedel-Crafts catalysts such as aluminum chloride and zinc chloride, and solid Lewis acids generally. Again, what is important is that processes and catalysts for alkylation are well known to those skilled in the alkylation art and need not be described here in great detail. It is important to emphasize that the nature of the alkylation process and catalyst is not critical to the success of our invention and is largely a matter of choice to be made by the practitioner.

The selective alkylation zone produces a selective alkylation zone effluent that enters separation facilities for the recovery of products and recyclable feed compounds. Suitable fractionation facilities for such separations which are well known by those skilled in the art and can be tailored as desired to provide specific fractions and purities are described in U.S. Pat. Nos. 3,950,448; 4,237,327; 4,237,328; and 5,012,021. In one commonly employed arrangement, the bottoms stream of the HF stripping column where the alkylation catalyst is HF, or the selective alkylation zone effluent stream where the alkylation catalyst is a solid alkylation catalyst, passes into a benzene column which produces an overhead stream containing benzene and a bottoms stream containing the alkylate product. This bottoms stream passes into a paraffin column which produces an overhead liquid stream containing unreacted paraffins, which normally is recycled as a recycle stream to the dehydrogenation zone, and a bottoms stream containing the product alkylate and any higher molecular weight side product hydrocarbons formed in the selective alkylation zone. This bottoms steam is passed into a rerun column which produces an overhead alkylate product stream containing the detergent alkylate and a bottoms stream containing polymerized olefins and polyalkylated benzenes (heavy alkylate).

A common variant of the subject process includes the selective hydrogenation of diolefins that are normally present in the dehydrogenated product stream or the stripping effluent stream. It is well known that diolefins are formed during the catalytic dehydrogenation of paraffins. Selective diolefin hydrogenation converts the diolefins to monoolefins, which are the desired product of the dehydrogenation section, and produces a selective diolefin hydrogenation product stream.

Another common variant of the subject process includes the selective hydrogenation of monoolefins that are normally present in the overhead liquid stream of the paraffin column. It is well known that unreacted monoolefins from the selective alkylation zone are present in the overhead liquid stream, and that these monoolefins shorten the life of currently available dehydrogenation catalysts where the overhead liquid stream is recycled to the dehydrogenation zone. Selective monoolefin hydrogenation converts the monoolefins to paraffins, which are the desired feed compound of the dehydrogenation section, and produces a selective monoolefin hydrogenation product stream.

We shall now describe the improvement which is our invention. Our invention eliminates or significantly reduces the aromatic by-products in the feedstock to the selective alkylation zone in the prior art processes for the production of alkylated aromatic compounds. Our invention reduces the deactivation rate of solid alkylation catalyst and, thereby, produces a significantly higher yield of linear alkylated aromatic compounds than the prior art processes.

It is well known that aromatic by-products are formed during the catalytic dehydrogenation of paraffins. For instance, the article starting at page 86 of the Jan. 26, 1970 issue of "Chemical Engineering" states that the product of the dehydrogenation of linear paraffins includes aromatic compounds. The nature of the particular aromatic by-products that are formed in dehydrogenation is not essential to this invention. Without limiting this invention in any way, these aromatic by-products are believed to include, for example, alkylated benzenes, naphthalenes, other polynuclear aromatics, alkylated polynuclear hydrocarbons in the $C_{10}$-$C_{15}$ range, indanes, and tetralins, that is, they are aromatics of the same carbon number as the paraffin being dehydrogenated and may be viewed as aromatized normal paraffins. Some aromatic by-products may be more detrimental than others in deactivating solid alkylation catalysts. It is believed that aromatic by-products with few or small alkyl groups are more detrimental to solid alkylation catalysts than aromatic by-products with multiple or long alkyl groups. It is also believed that aromatic by-products having multiple aromatic rings are more detrimental to solid alkylation catalysts than aromatic by-products having single aromatic rings. The particular side reactions that lead to the formation of the aromatic by-products are also not essential to this invention. Again, without limiting this invention in any way, an illustration of some of the parallel thermal cracking reactions that can lead to the formation of aromatic by-products is found in the diagram at the top of page 4–37 of the book mentioned above entitled "Handbook of Petroleum Refining Processes". Typically, from about 0.2 to about 0.7 weight percent, and generally to the extent of no more than 1 weight percent, of the feed paraffinic compounds to a dehydrogenation zone form aromatic by-products. Although some commercially available dehydrogenation catalysts are more selective than others at minimizing the formation of aromatic by-products, it is believed that these by-products are formed at least to a small extent at suitable dehydrogenation conditions in the presence of most if not all commercially available dehydrogenation catalysts. Since it is an economic advantage to operate the dehydrogenation zone at conditions that produce a high conversion of the feed paraffinic compounds and a high yield of the desired olefins, these aromatic by-products are produced at least to a small extent in most if not all commercial dehydrogenation zones.

The aromatic by-products from the dehydrogenation section enter the alkylation section. In the selective alkylation zone containing a solid alkylation catalyst, several possibilities can then occur. First, some of the aromatic by-products deposit on the surface of the catalyst and as mentioned above deactivate the catalyst. Second, as mentioned above some of the aromatic by-products are alkylated by monoolefins to form heavy alkylate. Each mole of heavy alkylate formed by this route represents the loss of two moles of feed paraffinic compound toward the production of a less-valuable product and reduces both dehydrogenation selectivity and alkylation selectivity. Third, some of the aromatic by-products pass through the selective alkylation zone unreacted, are recovered with the overhead liquid stream of the paraffin column which is recycled to the dehydrogenation zone, and ultimately accumulate to unacceptable concentrations. In the prior art processes employing a solid alkylation catalyst, the concentration of aromatic by-products in the stripping effluent stream can typically accumulate to 4-10 weight percent, which leads to rapid deactivation of solid alkylation catalyst. Where the alkylation catalyst is HF in the prior art processes, the concentration of aromatic by-products in the stripping effluent stream can typically accumulate to 3-6 weight percent. Although it would be desirable to remove the aromatic by-products in the alkylate recovery zone, the difficulty of separating the aromatic by-products from the unreacted paraffins and unreacted monoolefins all of the same carbon number precludes such an arrangement.

Our invention achieves the objectives set forth above by selectively removing at least a portion of the aromatic by-products in the dehydrogenated product stream using at least one aromatics removal zone. An aromatics removal zone may be placed in one or more locations in the prior art processes. First, the aromatic by-products may be selectively removed from the dehydrogenated product stream and the stripping effluent stream. Second, where the overhead liquid stream of the paraffin column is recycled to the dehydrogenation zone, which is normally the case in commercial applications, the aromatic by-products may be selectively removed from the recycle stream. Third, where the subject process includes a selective monoolefin hydrogenation zone, the aromatic by-products may be selectively removed from the selective monoolefin hydrogenation product stream. Fourth, where the subject process includes a selective diolefin hydrogenation zone, the aromatic by-products may be selectively removed from the selective diolefin hydrogenation product stream. The aromatics removal zone is preferably located between the dehydrogenation zone and the selective alkylation zone because the aromatic by-products are preferably selectively removed prior to entering the selective alkylation zone. These locations set forth above are not necessarily equivalent in terms of the required equipment, such as heaters, heat exchangers, vessels, coolers, and etc., to practice our invention. Those skilled in the art of hydrocarbon processing are able to design and provide the required equipment.

Suitable aromatics removal zones may be selected from any processing methods which exhibit the primary requirement of selectivity for the aromatic by-products. Suitable aromatics removal zones include, for example, sorptive separation zones and liquid-liquid extraction zones. However, it should be recognized that a particular aromatics removal zone may give better results than another zone. The preferred aromatics removal zone is a sorptive separation zone.

Where the aromatics removal zone is a sorptive separation zone, our invention can be practiced in fixed bed or moving sorbent bed systems, but the fixed bed system is preferred. The sorbent may be installed in one or more vessels and in either series or parallel flow. The flow of the stream containing the aromatic by-products through the sorptive separation zones is preferably performed in a parallel manner so that when one of the sorbent beds or chambers is spent by the accumulation of the aromatic by-products thereon, the spent zone may be by-passed while continuing uninterrupted operation through the parallel zone. The spent zone of sorbent may then be regenerated or the spent sorbent may be replaced as desired.

Our invention may also be practiced in a cocurrent, pulsed batch process, like that described in U.S. Pat. No. 4,159,284 or in a cocurrent, pulsed continuous process, like that disclosed in U.S. Pat. Nos. 4,402,832 and 4,478,721, both issued to Gerhold.

Our invention may also be practiced in a countercurrent simulated moving bed system, such as described in U.S. Pat. No. 2,985,589 issued to Broughton. Cyclic advancement of the input and output streams can be accomplished by manifolding systems, which are also known, e.g., by rotary disc valves shown in U.S. Pat. Nos. 3,040,777 and 3,422,848. Equipment utilizing these principles are familiar, in sizes ranging from pilot plant scale, such as described in U.S. Pat. No. 3,706,812 issued to deRosset, to commercial scale in flow rates from a few cc per hour to many thousands of gallons per hour.

Suitable sorbents may be selected from materials which exhibit the primary requirement of selectivity for the aromatic by-products and which are otherwise convenient to use. Suitable sorbents include, for example, molecular sieves, silica, activated carbon, activated charcoal, activated alumina, silica-alumina, clay, cellulose acetate, synthetic magnesium silicate, macroporous magnesium silicate, and/or macroporous polystyrene gel. It should be understood that the above-mentioned sorbents are not necessarily equivalent in their effectiveness. The choice of sorbent will depend on several considerations including the capacity of the sorbent to retain aromatic by-products, the selectivity of the sorbent to retain the aromatic by-products which are more detrimental to solid alkylation catalysts, and the cost of the sorbent. The preferred sorbent is a molecular sieve, and the preferred molecular sieve is 13X zeolite (sodium zeolite X). Detailed descriptions of zeolites may be found in the book authored by D. W. Breck entitled "Zeolite Molecular Sieves" published by John Wiley and Sons, New York, in 1974.

Those skilled in the art are able to select the appropriate conditions for operation of the sorbent without undue experimentation. For example, a fixed bed sorptive separation zone containing 13X zeolite may be maintained at a temperature from about 20° C. to about 300° C. and preferably from about 100° C. to about 200° C., a pressure effective to maintain the stream containing the aromatic by-products in a liquid phase at the chosen temperature, and a liquid hourly space velocity from about 1 hr$^{-1}$ to about 10$^{-1}$ and preferably from about 1 hr$^{-1}$ to about 3 hr$^{-1}$. The flow of the stream containing the aromatic by-products through the sorptive separation zone may be conducted in an upflow, downflow or radial-flow manner.

Although both liquid and vapor phase operations can be used in many sorptive separation processes, liquid phase operation is preferred for the sorptive separation zone of our invention because of the lower temperature requirements and because of the higher sorption yields of the aromatic by-products that can be obtained with liquid phase operation over those obtained with vapor phase operation. Therefore, the temperature and pressure of the sorptive separation zone during sorption of the aromatic by-products are preferably selected to maintain in a liquid phase the stream from which the aromatic by-products are selectively removed. Alternatively, the temperature and pressure of the sorptive separation zone during sorption of the aromatic by-products can be selected to maintain in a liquid phase the aromatic by-products in the stream from which the aromatic by-products are selectively removed. Mixed phases (i.e., a combination of a liquid phase and a vapor phase) for the stream from which the aromatic by-products are separated are generally not preferred because of the well-known difficulties involved in maintaining uniform flow distribution of both a liquid phase and a vapor phase through a sorptive separation zone. The resulting unsorbed stream having a reduced concentration of aromatic by-products is then passed on in the process. However, the operating conditions of a sorptive separation zone can be optimized by those skilled in the art to operate over wide ranges, which are expected to include the conditions in the reaction zones of our invention and its variants. Therefore, an embodiment of our invention includes a sorptive separation zone contained in a common reaction vessel with the dehydrogenation zone, the selective diolefin hydrogenation zone, the selective alkylation zone, or the selective monoolefin hydrogenation zone.

Following an appropriate processing period which will depend on the composition of the stream containing the aromatic by-products and the particular aromatic by-products themselves, it is usually necessary to regenerate the sorbent, that is to remove the sorbed aromatic by-products from the sorbent so that the sorbent may be reused. There are numerous methods of regenerating the sorbent. It is not intended to limit this invention to any particular method of regenerating the sorbent. Any suitable regeneration method may be used, including:

(a) altering the temperature and pressure of the sorbent to vaporize the sorbed aromatic by-products which are then condensed;
(b) altering the temperature and pressure of the sorbent and treating with a gas or a vapor to displace the sorbed aromatic by-products which are then condensed;
(c) altering the temperature and pressure of the sorbent and treating with a liquid to displace or desorb the sorbed aromatic by-products;
(d) altering the temperature and pressure of the sorbent and treating with a vapor or gas and a liquid to displace or desorb the sorbed aromatic by-products; and
(e) burning, that is oxidizing the sorbed aromatic by-products into carbon dioxide and water, where the sorbent can be subjected to high temperature (for example, alumina).

Suitable vapors or gases and liquids may be selected from materials which exhibit the primary requirement of displacing the aromatic by-products from the sorbent and which are otherwise convenient to use. Suitable gases or vapors include, for example, steam, nitrogen, hydrogen, a hydrogen-rich gas stream and/or light hydrocarbons, and mixtures thereof. As used herein, the term "rich" is intended to indicate a molar concentration of the indicated compound or class of compounds above 50%. A hydrogen-rich gas stream is available as a product stream from the dehydrogenation zone. Suitable liquids include, for example, lighter aromatic hydrocarbons including benzene, water, and/or lighter paraffins and olefins, including $C_6$ to $C_9$ paraffins and olefins, and mixtures thereof. Suitable combinations of vapors or gases and liquids include hydrogen gas and benzene liquid, a hydrogen-rich gas and benzene liquid and benzene vapor and benzene liquid. The vapor and liquid may be of the same composition. It should be understood that the above mentioned vapors or gases and liquids are not necessarily equivalent in their effectiveness at desorbing the aromatic by-products. In a preferred method of regeneration, a wash of a mixture of liquid benzene and liquid $C_6$ to $C_{10}$ paraffins at desorbing conditions of temperature and pressure may be used.

It should be understood that in certain methods of regeneration it is also necessary to remove the regenerating medium from the sorbent before normal processing is resumed. This is particularly true if water has been employed to displace the sorbed aromatic by-products. The water may be conveniently removed from the sorbent by a drying procedure, e.g. by passing a stream of warm air or gas through the sorptive separation zone.

Those skilled in the art are able to select the appropriate conditions for regeneration of the sorbent without undue experimentation. For example, a fixed bed sorptive separation zone containing $13\times$ zeolite may be regenerated using a desorbent mixture of 30 vol. % liquid benzene and 70 vol. % liquid decane at desorption conditions including a temperature from about 20° C. to about 300° C. and preferably from about 100° C. to about 200° C., a pressure of from atmospheric pressure to a pressure effective to maintain the desorbent mixture in a liquid phase at the chosen temperature, and a liquid hourly space velocity from about 1 hr$^{-1}$ to about 10 hr$^{-1}$ and preferably from about 1 hr$^{-1}$ to about 3 hr$^{-1}$. The flow direction of the desorbent mixture through the sorptive separation zone may be upflow or radial-flow, but the preferred direction is downflow. The phase of the desorbent mixture through the sorptive separation zone may be liquid phase, vapor phase, or a mixture of liquid and vapor phases.

Where the aromatics removal zone is a liquid-liquid extraction zone, our invention can be practiced by contacting the stream containing the aromatic by-products with a suitable solvent which selectively retains the aromatic by-products. Organic compounds suitable for use as part of the solvent composition include the aliphatic and cyclic alcohols, cyclic monomeric sulfones, the glycols and glycol ethers, as well as the glycol esters and glycol ether esters, but the preferred organic compound is a sulfolane. Typically, organic compounds belonging to the sulfolane class are 2-sulfolene, 2-methyl sulfolane, 2,3-dimethylsulfolane, 2,4-dimethyl-4-sulfolane, methyl-3-sulfonyl ether, ethyl-3-sulfonyl sulfide, and others. Our invention may be practiced using any conventional or convenient type of apparatus known to those skilled in the art. Also the operation conditions suitable for the practice of our invention are conventional. Generally, the amount of solvent composition utilized in admixture with an appropriate feedstock should be at least sufficient to dissolve the constituents to be extracted. It may be desirable to use a considerable excess over the theoretical amount of solvent composition necessary especially when maximum purity and maximum recovery of aromatic by-products is required. Usually, in the extraction step, the solvent composition to feed ratios will range from about 1:1 to about 20:1 volume, preferably, from about 3:1 to about 15:1 by volume. A summary of the conditions necessary for the practice of the sulfolane type of solvent operation may be found in Petroleum Refiner, Volume 38, No. 9, September 1959, pages 185-192. Liquid-liquid extraction processes for removal and recovery of aromatic hydrocarbons from mixed hydrocarbon feeds are described in U.S. Pat. No. 3,433,735 issued to Broughton, U.S. Pat. No. 3,466,345 issued to De Graff, and U.S. Pat. No. 3,642,614 issued to Van Tassel.

The following Examples illustrate the effect of removing the aromatic by-products.

EXAMPLES

All alkylation pilot plant tests were conducted in a fixed bed reactor containing a solid alkylation catalyst at 120° C. unless otherwise stated. The benzene-to-olefin feed molar ratio was maintained at 25, pressure at 250 psig, and 2 hr$^{-1}$ LHSV. The fresh (untreated) alkylation section feed was obtained from a commercial LAB process having a dehydrogenation section, a selective diolefin hydrogenation section, and an alkylation section using HF acid catalyst. The composition given in Table 1 is typical of alkylation section feeds from commercial LAB processes with continuous alkylation and paraffin recycle to the dehydrogenation section. Olefin conversion was monitored by gas chromatographic analysis of the product. The n-paraffins were used as an internal standard for calculating conversion at each carbon number.

EXAMPLE 1

Aromatic by-products were removed from the commercial alkylation section feed (Feed 1) as described below. Feed 2 was prepared by passing the commercial alkylation section feed continuously over a fixed sorptive bed of 13X molecular sieves. The bed was maintained at 130° C. and 450 psig to maintain liquid phase. The liquid hourly space velocity was about 2.7 hr$^{-1}$. The experiment was continued until a certain concentration of aromatic by-products was observed in the bed effluent by gas chromatography. Regeneration of the 13X sieves was accomplished by benzene flush at the same conditions. This process was repeated until a sufficient amount of treated feed was available for testing in an alkylation pilot plant. Treating the feed in this manner reduced the aromatic by-products from 5.2 to 2.1 wt. % of the treated alkylation section feed. Feed 3 was prepared by adding the 13X sieve directly into a vessel containing Feed 1. A 50% excess of sieves was used based on the capacity of the sieves determined experimentally. The contents were then stirred at room temperature and atmospheric pressure for about 10 minutes. The liquid and solid were separated by filtration and the liquid product was found to have 0.3 wt. % aromatics content. Feed 4 was prepared by blending appropriate amounts of Feed 1 and Feed 3 to obtain 1.0 wt. % aromatics content.

Table 2 lists the analyses of the four feeds for total aromatics. The analyses also showed no differences in olefin content among the four feeds.

Table 2 shows results of alkylation pilot plant tests of these four feeds. The catalyst used in these test is a fluorided amorphous silica-alumina, however the choice of solid alkylation catalyst is not believed to be important in demonstrating the effect of aromatic by-products removal. Catalyst life, as defined by hours at 100% olefin conversion, increases from 16 hours (Feed 1), to 32 (Feed 2), to 46 (Feed 4), to 100 (Feed 3) hours with decreasing amounts of aromatic feed by-products. Additionally, removing aromatic by-products leads to increased selectivity to monoalkylbenzene from 87.8 to 93.5 wt. %. This increase is believed to occur because benzene is alkylated by the olefins to the desired product instead of the aromatic by-products being alkylated by the olefins to yield an undesirable material. The table shows no significant change in linearity (about 94%) with aromatic by-products removal.

EXAMPLE 2

Two experiments were conducted to remove aromatic by-products from a commercial alkylation section feed. Sulfolane and ethylenediamine were evaluated as solvents to extract the aromatic by-products. Experiments were conducted at room temperature and atmospheric pressure. One volume of alkylation section feed was extracted with one volume of solvent. After mixing and phase separation, a sample of the hydrocarbon was analyzed for aromatic by-products. The remaining volume of extracted hydrocarbon was extracted a second time with an equal volume of fresh solvent. The separation and analysis were repeated. The results are listed below.

|  | % Aromatic By-Products | |
|---|---|---|
|  | Sulfolane | Ethylenediamine |
| Untreated Feed | 4.9 | 4.9 |
| After 1 Extraction | 3.7 | 4.0 |
| After 2 Extractions | 2.7 | 3.3 |

Both solvents have some capability of removing aromatic by-products from the alkylation section feed. However, other solvents may be more effective than these in removing aromatic by-products. These two experiments demonstrate that the aromatic by-products can be extracted from the alkylation feed by liquid-liquid extraction. There is no evidence by gas chromatographic analyses that any olefin is lost in either solvent.

TABLE 1

| Commercial Alkylation Section Feed Composition | |
|---|---|
| Linear Paraffins & Olefins | Wt. % |
| $C_{10}$ | 13.7 |
| $C_{10}=$ | 1.7 |
| $C_{11}$ | 26.1 |
| $C_{11}=$ | 3.5 |
| $C_{12}$ | 22.2 |
| $C_{12}=$ | 3.3 |
| $C_{13}$ | 14.9 |
| $C_{13}=$ | 2.8 |
| $C_{14}$ | 5.1 |
| $C_{14}=$ | 0.1 |
| Aromatics | 5.2 |

TABLE 1-continued

| Commercial Alkylation Section Feed Composition | |
|---|---|
| Linear Paraffins & Olefins | Wt. % |
| Others | 1.4 |

TABLE 2

Effect of Aromatics Removal
(120° C., B/O = 25, 2 LHSV, 500 psig)

| Feed No. | Wt. % Aromatics Dehydrogenation Feed | % Aromatics Removal | Hours At 100% Conversion | % Linearity | Wt. % Monoalkylate Selectivity |
|---|---|---|---|---|---|
| 1 | 5.2 | 0 | 16 | 93.9 | 87.8 |
| 2 | 2.1 | 59.6 | 32 | 94.4 | 90.2 |
| 4 | 1.0 | 80.8 | 46 | 94.2 | 92.2 |
| 3 | 0.3 | 94.2 | 100 | 94.0 | 93.5 |

EXAMPLE 3

In a commercial LAB process consisting of a dehydrogenation section, a selective diolefin hydrogenation section, and an alkylation section, the concentration of aromatic by-products may be 6.7% by weight in the recycle stream and 6.4% by weight in the stripping effluent stream without the use of an aromatics removal zone. If the recycle stream were passed in a continuous and uninterrupted manner through a sorptive separation zone containing silica-alumina to remove aromatic by-products, the aromatic by-products in the sorptive separation zone effluent stream may be reduced to a concentration of less than about 0.5% by weight on a continuous basis. As a consequence, the aromatic by-products in the stripping effluent stream may be reduced and the life of the alkylation catalyst may be significantly increased.

EXAMPLE 4

In a commercial LAB process consisting of a dehydrogenation section, a selective diolefin hydrogenation section, an alkylation section and a selective monoolefin hydrogenation section, the selective diolefin hydrogenation section may be located between the product separator and the stripping column of the dehydrogenation section. The concentration of aromatic by-products may be 5.0% by weight in the stripping effluent stream without the use of an aromatics removal zone. The stripping effluent stream may be passed through a sorptive separation zone containing a molecular sieve to remove aromatic by-products in an non-continuous and intermittent manner. When the sorptive separation zone is in operation, the aromatic by-products in the sorptive separation zone effluent stream may be reduced to a concentration of less than about 0.5% by weight or even less. Then the sorptive separation zone may be taken out of service and the concentration of aromatic by-products in the stripping effluent stream may be allowed to accumulate to a concentration of about 1.5% by weight. Then, the sorptive separation zone may be placed back in operation. Thus, the sorptive separation zone may be placed in operation and subsequently taken out of operation in a repetitive manner. As a consequence, the aromatic by-products in the stripping effluent stream may be reduced and maintained at a low concentration.

EXAMPLE 5

In a commercial LAB process consisting of a dehydrogenation section, a selective diolefin hydrogenation section, an alkylation section and a selective monoolefin hydrogenation section, the selective diolefin hydrogenation section may be located between the product separator and the stripping column of the dehydrogenation section. The concentration of aromatic by-products may be 8.8% by weight in the selective monoolefin hydrogenation section effluent and 8.5% by weight in the stripping effluent stream. If the effluent of the selective monoolefin hydrogenation section were continuously passed through a liquid-liquid extraction zone containing sulfolane to remove aromatic by-products, the aromatic by-products in the liquid-liquid extraction zone effluent stream may be reduced to a concentration of less than about 0.5% by weight on a continuous basis. As a consequence, the aromatic by-products in the stripping effluent stream may be reduced and the life of the alkylation catalyst may be significantly increased.

The above results show that aromatic by-products removal can be used to improve the operation of an alkylation section using a solid alkylation catalyst by extending the catalyst life at a particular operating temperature with a substantial increase in monoalkylate selectivity. One embodiment in accord with our invention is to remove at least a portion of the aromatic by-products in the stripping effluent stream to reduce the concentration of the aromatic by-products in the stripping effluent stream to less than 2 weight percent aromatic by-products. In a more specific embodiment, the concentration of aromatic by-products is reduced to less than about 1 weight percent. In a more specific embodiment, the concentration of aromatic by-products is reduced to less than about 0.5 weight percent.

A complete operation of the process can be more fully understood from a process flow for a preferred embodiment.

Referring now to the drawing, a paraffin feed stream comprising an admixture of $C_{10}-C_{15}$ normal paraffins is charged to line 1. The normal paraffins are combined with a stream of recycle paraffins from line 3. The paraffins are admixed with hydrogen from line 2 and other normal paraffins from line 3 and passed through line 5. A mixture of paraffins and hydrogen flowing through line 5 is first heated in the indirect heat exchanger 6 and is then passed into a fired heater 7. The resultant vapor phase mixture of paraffins and hydrogen is passed through line 8 into a dehydrogenation reactor 9. Inside the reactor 9, the paraffins are contacted in the presence of a dehydrogenation catalyst at conditions which effect the conversion of a significant amount of the paraffins to the corresponding olefins. There is thus produced a reactor effluent stream carried by line 10 which comprises a mixture of hydrogen, unreacted paraffins, monoolefins, diolefins, $C_9$-minus hydrocarbons, and aromatic hydrocarbons. This reactor effluent stream is first cooled by indirect heat exchange in the heat exchanger 6 and is then further cooled in the indirect heat exchange means 11. This cooling is sufficient to condense substantially all of the $C_{10}$-plus hydrocarbons into a liquid phase stream and separate the liquid phase stream from the remaining vapor, which is rich in hydrogen. This reactor effluent stream enters the vapor-liquid separation vessel 12 wherein it is divided into a hydrogen-rich vapor phase stream removed through line 13 and a dehydrogenated product stream removed through line 14. The vapor phase stream is divided into a net hydrogen product stream removed through line 30 and a hydrogen stream that is recycled by line 4.

The dehydrogenated product stream removed from the bottom of the separator 12 contains unreacted paraffins, a major amount of monoolefins, and minor amounts of $C_9$-minus hydrocarbons, diolefins, and aromatic by-products, and some dissolved hydrogen. As used herein, the term "a major amount of monoolefins" is intended to indicate a molar concentration of the monoolefins above 5%; the term "a minor amount of $C_9$-minus hydrocarbons" is intended to indicate a molar concentration of the $C_9$-minus hydrocarbons below 2%; the term "a minor amount of diolefins" is intended to indicate a molar concentration of the diolefins below 2%; and the term "a minor amount of aromatic by-products" is intended to indicate a molar concentration of the aromatic by-products below 10%. The dehydrogenated product stream, which is the liquid phase portion effluent of the separator, is then passed through line 14 to a stripping column 19. In this column, the $C_9$-minus hydrocarbons produced in the dehydrogenation reactor as by-products and any remaining dissolved hydrogen are separated from the $C_{10}$-plus hydrocarbons and concentrated into a net overhead stream removed from the process through line 20.

The remainder of the hydrocarbons entering the stripping column are concentrated into a stripping effluent stream carried by line 21. The stripping effluent stream is then passed into an aromatics removal zone 23. In this zone, the stripping effluent stream is contacted with a sorbent under conditions which promote the removal of the aromatic by-products.

The effluent from the aromatics removal zone is transferred via a line 24. This stream comprises an admixture of the unreacted paraffins and the monoolefins and has a greatly reduced concentration of aromatic by-products compared to the dehydrogenation reactor effluent. This admixture is combined with benzene from line 25 and passed into an alkylation reactor 26 through line 27. In the alkylation reactor, benzene and the olefins are admixed in the presence of an alkylation catalyst at alkylation-promoting conditions.

The alkylation reactor effluent stream carried by a line 28 and passed into a benzene fractionation column 27' by a line 28. This stream comprises an admixture of unreacted benzene, unreacted paraffins, and the product alkylated benzene compounds. This stream is separated in column 27' into a bottoms stream and an overhead stream comprising hydrogen, trace amounts of light hydrocarbons, and the unreacted benzene. The overhead stream is carried by a line 29 to a separator drum 31 from which hydrogen and light gases are removed via a line 32 and condensed liquid is withdrawn by a line 33 to supply reflux to column 27' and benzene for recycle by a line 25. A line 34 carries the remainder of the alkylation reactor effluent stream from column 27' to a paraffin column 35 from which a bottoms stream containing the alkylated benzene compounds and heavy alkylate by-products is taken by a line 36. The contents of line 36 are separated by a rerun column 37 into a bottoms stream 38 comprising heavy alkylate and an overhead alkylate product stream 39 containing the alkylated benzene compounds. Overhead from paraffin column 35 is a recycle stream that contains a mixture of paraffins that are recycled to the dehydrogenation zone via line 3.

The Figure shows a preferred arrangement for the integrated dehydrogenation-alkylation scheme of this invention. This description is not meant to preclude other arrangements for the process flow of this invention.

What is claimed is:

1. In a process of producing an alkylated aromatic compound by:
   (a) dehydrogenating a feed stream containing $C_6$–$C_{22}$ paraffins in a dehydrogenation zone and recovering therefrom a dehydrogenated product stream containing in addition to unreacted paraffins a major amount of monoolefins and minor amounts of $C_9$-minus hydrocarbons, diolefins and aromatic by-products;
   (b) optionally selectively hydrogenating to monoolefins at least a portion of the diolefins in the dehydrogenated product stream in a selective diolefin hydrogenation zone and recovering therefrom a selective diolefin hydrogenation product stream containing unreacted paraffins, a major amount of the monoolefins and minor amounts of the $C_9$-minus hydrocarbons and the aromatic by-products;
   (c) passing at least one of
      (i) the selective diolefin hydrogenation product stream where present; and
      (ii) the dehydrogenated product stream through a stripping separation zone to remove the $C_9$-minus hydrocarbons and recovering therefrom a stripping effluent stream containing the unreacted paraffins, a major amount of the monoolefins, and a minor amount of the aromatic by-products;
   (d) selectively alkylating an aromatic compound by reacting the aromatic compound and the monoolefins of the stripping effluent stream in a selective alkylation zone containing an alkylation catalyst to form principally alkylated aromatic compounds;
   (e) recovering from the selective alkylation zone an alkylate product stream containing the alkylated aromatic compounds and a recycle stream containing the unreacted paraffins, unreacted monoolefins, and a minor amount of the aromatic by-products;
   (f) optionally selectively hydrogenating to paraffins the unreacted monoolefins in the recycle stream in a selective monoolefin hydrogenation zone and recovering therefrom a selective monoolefin hydrogenation product stream containing the unreacted paraffins and a minor amount of the aromatic by-products; and
   (g) optionally recycling at least a portion of at least one of the selective monoolefin hydrogenation product stream where present and the recycle stream to the dehydrogenation zone;
   the improvement comprising selectively removing at least a portion of the aromatic by-products from at least one of the dehydrogenated product stream, the selective diolefin hydrogenation product stream, the stripping effluent stream, the recycle stream, and the selective monoolefin hydrogenation product stream in at least one aromatic by-products removal zone at conditions effective to selectively remove the aromatic by-products and reduce the concentration of the aromatic by-products in the stripping effluent stream to a level no more than about 2 weight percent.

2. The process of claim 1 where the alkylation catalyst comprises at least one from the group consisting of a solid alkylation catalyst and HF.

3. The process of claim 2 where the alkylation catalyst is a solid alkylation catalyst.

4. The process of claim 3 where the solid alkylation catalyst is selected from the group consisting of amorphous silica-alumina, zeolite, molecular sieve, pillared clay, sulfonated zirconia, aluminum chloride, and zinc chloride.

5. The process of claim 1 where the concentration of aromatic by-products in the stripping effluent stream is reduced to less than about 1 weight percent.

6. The process of claim 5 where the concentration of aromatic by-products in the stripping effluent stream is reduced to less than about 0.5 weight percent.

7. The process of claim 1 where the aromatic by-products removal zone is a sorptive separation zone or a liquid-liquid extraction zone.

8. The process of claim 7 where the aromatic by-products removal zone is a sorptive separation zone.

9. The process of claim 8 where the sorptive separation zone contains at least one member of the group consisting of activated carbon, silica, activated alumina, activated charcoal, silica-alumina, clay, silica gel, cellulose acetate, synthetic magnesium silicate, macroporous magnesium silicate, macroporous polystyrene gel, and a molecular sieve.

10. The process of claim 9 where the sorptive separation zone contains a molecular sieve.

11. The process of claim 10 where the molecular sieve is 13X zeolite.

12. The process of claim 8 further characterized in that the sorptive separation zone and at least one of the dehydrogenation zone, the selective diolefin hydrogenation zone, the selective alkylation zone, and the selective monoolefin hydrogenation zone are contained in a common reaction vessel.

13. The process of claim 7 where the aromatic by-products removal zone is a liquid-liquid extraction zone.

14. The process of claim 13 further characterized in that the liquid-liquid extraction zone contains a sulfolane.

15. The process of claim 1 where the feed stream contains $C_{10}$–$C_{22}$ linear paraffins.

16. The process of claim 15 where the feed stream contains $C_{15}$–$C_{20}$ linear paraffins.

17. The process of claim 15 where the feed stream contains $C_{10}$–$C_{15}$ linear paraffins.

18. The process of claim 15 where the feed stream contains at least one $C_{10}$-plus linear paraffin.

19. The process of claim 1 where the aromatic compound is selected from the group consisting of benzene, toluene, xylene, and mixtures thereof.

20. The process of claim 1 where at least a portion of the alkylated aromatic compounds are monoalkylated aromatic compounds.

21. The process of claim 1 further characterized in that the conditions are effective to maintain in a liquid phase the stream from which the aromatic by-products are selectively removed.

22. The process of claim 1 further characterized in that the conditions are effective to maintain in a liquid phase the aromatic by-products in the stream from which the aromatic by-products are selectively removed.

23. The process of claim 1 further characterized in that the conditions include a temperature of from about 20° to about 300° C.

24. The process of claim 1 further characterized in that the conditions include a liquid hourly space velocity of from about 1 to about 10 $hr^{-1}$.

25. In a process of producing a monoalkylated aromatic compound by:
(a) dehydrogenating a feed stream containing $C_{10}$–$C_{15}$ paraffins in a dehydrogenation zone and recovering therefrom a dehydrogenated product stream containing in addition to unreacted paraffins a major amount of monoolefins and minor amounts of $C_9$-minus hydrocarbons, diolefins and aromatic by-products;
(b) selectively hydrogenating to monoolefins at least a portion of the diolefins in the dehydrogenated product stream in a selective diolefin hydrogenation zone and recovering therefrom a selective diolefin hydrogenation product stream containing unreacted paraffins, a major amount of the monoolefins and minor amounts of the $C_9$-minus hydrocarbons and the aromatic by-products;
(c) passing at least a portion of the selective diolefin hydrogenation product stream through a stripping separation zone to remove the $C_9$-minus hydrocarbons and recovering therefrom a stripping effluent stream containing the unreacted paraffins, a major amount of the monoolefins, and a minor amount of the aromatic by-products;
(d) selectively monoalkylating benzene by reacting the monoolefins in the stripping effluent stream with benzene in a selective monoalkylation zone containing an alkylation catalyst to form principally monoalkylated benzene compounds;
(e) recovering from the selective monoalkylation zone a monoalkylate product stream containing the monoalkylated benzene compounds and a recycle stream containing the unreacted paraffins, unreacted monoolefins, and a minor amount of the aromatic by-products; and
(f) recycling at least a portion of the unreacted paraffins in the recycle stream to the dehydrogenation zone;

the improvement comprising selectively removing at least a portion of the aromatic by-products from the stripping effluent stream in at least one aromatic by-products removal zone at conditions including a temperature of from about 20° to about 300° C., a pressure effective to maintain the dehydrogenated product stream in a liquid phase and a liquid hourly space velocity of from about 1 to about 10 $hr^{-1}$.

* * * * *